US000001311H

United States Statutory Invention Registration [19]

[11] Reg. Number: H1311

Nakamura et al.

[43] Published: May 3, 1994

[54] METHANOL SYNTHESIS PROCESS

[76] Inventors: Tadasi Nakamura; Kinya Tsuji; Yoriko Obata, all of c/o Mitsubishi Gas Chemical Company, Inc. Niigata Research Laboratory 182, Shinwari, Tayuhama, Niigata-shi Niigata-ken, Japan

[21] Appl. No.: 999,569

[22] Filed: Dec. 30, 1992

Related U.S. Application Data

[60] Continuation of Ser. No. 787,671, Nov. 4, 1991, abandoned, which is a division of Ser. No. 698,364, May 9, 1991, Pat. No. 5,089,452, which is a continuation-in-part of Ser. No. 607,842, Nov. 1, 1990, abandoned, which is a continuation of Ser. No. 448,066, Dec. 8, 1989, abandoned.

[30] Foreign Application Priority Data

Feb. 9, 1989 [JP] Japan ..... 1-28774

[51] Int. Cl.[5] ..... C07C 27/06

[52] U.S. Cl. ..... 518/713

[58] Field of Search ..... 518/713

[56] References Cited

U.S. PATENT DOCUMENTS 3,971,735 7/1976 Asano et al. ..... 518/713

FOREIGN PATENT DOCUMENTS 2542325 9/1984 France .

242827 2/1987 German Democratic Rep. .

*Primary Examiner*—Shean Wu

[57] ABSTRACT

A methanol synthesis process comprising reacting a methanol synthesis gas composition in the presence of a methanol synthesis catalyst. The methanol synthesis catalyst is a catalyst produced by drying and sintering a catalyst precursor. The catalyst precursor is produced from a copper compound, a zinc compound, an aluminum compound and a boron compound, by (a) precipitating from an aqueous reaction mixture comprising a copper sulfate which is recovered from a copper etching waste solution mother liquor, the copper sulfate comprising up to 10% by weight of said mother liquor, with a precipitant, the precipitant being in an amount of 1-fold to 2-fold equivalent of the copper sulfate, the precipitating being carried out in the presence of the boron compound, the boron compound being a water soluble boron compound, and mixing therewith the zinc compound, without separation, to form a precipitate in the reaction mixture, (b) filtering the reaction mixture from step (a) to form a cake, (c) washing the cake from step (b) with an aqueous alkali solution in a concentration of 0.01 to 0.5 weight % and then washing with water, (d) adding the aluminum compound to the washed cake of step (c), (e) kneading the resulting mixture from step (d) and (f) drying the resulting kneaded mixture from step (e).

26 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHANOL SYNTHESIS PROCESS

This application is a continuation of application Ser. No. 07/787,671 filed Nov. 4, 1991, abandoned, which is a division application of Ser. No. 07/698,364 filed May 9, 1991 (now U.S. Pat. No. 5,089,452), which is a continuation-in-part application of Ser. No. 07/607,842 filed Nov. 1, 1990 (abandoned), which is a continuation of application Ser. No. 07/448,066 filed Dec. 8, 1989 (abandoned).

BACKGROUND OF THE INVENTION

1. Field of the invention

This invention relates to a method for preparing a catalyst precursor for use in methanol synthesis using, as a copper source, copper sulfate recovered from cheap copper etching waste solution.

2. Description of the Related Arts

As a copper source of a catalyst for methanol synthesis, copper nitrate or copper acetate which do not cause contamination of catalytic poison is employed in many cases. Thus, the total cost for preparing the catalyst becomes significantly high.

The present inventors' group previously provided a method of preparing a basic copper carbonate which is a catalyst precursor using cheap copper sulfate as a starting material in Japanese Patent Application Laid-Open No. 9809/1989.

The basic copper carbonate as a catalyst precursor obtained from copper sulfate according to the above method can be suitably employed for preparing a catalyst for methanol synthesis at low cost. However, from an industrial viewpoint, it is important to develop a method of preparing a catalyst precursor at a lower cost.

Recently, attention has been paid to the fact that copper sulfate recovered from etching waste solution is much cheaper than the conventional and commercially available copper sulfate. It has been required to develop techniques for utilizing the recovered copper sulfate as a source of copper for preparing a catalyst for use in methanol synthesis.

According to an investigation by the present inventors it wa found that copper sulfate recovered from a copper etching waste solution usually contains the mother liquor in the amount of more than 10%, and it cannot be used as the starting material for preparing a catalyst precursor without any treatment. That is, a large amount of excess sulfuric acid is contained in the copper etching waste solution, and various chemicals are also contained therein to control the etching rate or to improve the characteristics of the etching solution. Thus, it was found that these compounds have harmful influence to the final catalyst to be prepared.

In U.S. Pat. No. 4,659,555, there is disclosed a method of preparing a basic copper carbonate by using copper (II) chloride recovered from a copper etching waste solution. However, in the basic copper carbonate obtained by the above method, chlorine and sodium which become catalyst poisons in a methanol synthetic reaction are contained in amounts that exceed the allowable concentration. Therefore, the said basic copper carbonate is not suitable as a starting material for a methanol synthesis catalyst.

SUMMARY OF THE INVENTION

An object of the present invention is to provide a method of preparing a catalyst precursor for methanol synthesis using, as a copper source, copper sulfate recovered from a cheap copper etching waste solution.

The present inventors have intensively studied the utilization of copper sulfate recovered from very cheap copper etching waste solution as a starting material for preparing a catalyst for synthesizing methanol. It has been found that the amount of a mother liquor accompanying crystals of recovered copper sulfate largely affects the characteristics of the final catalyst and that the amount of mother liquor contained in the recovered copper sulfate should be kept to 10% or less.

The present invention provides a method of preparing a catalyst precursor for synthesizing methanol using copper sulfate recovered from a very cheap copper etching waste solution as the copper source, which comprises using recovered copper sulfate containing the mother liquor in the amount of 10% by weight or less, and combining a zinc compound and an aluminum compound, and optionally, and a boron compound with the recovered copper sulfate.

The copper sulfate recovered from the copper etching waste solution usually contains the mother liquor in the amount of more than 10%. Therefore, a desired catalyst having excellent properties cannot be obtained from the precipitates of the basic copper carbonate obtained by using the recovered copper sulfate without any treatment, even when the precipitates are washed carefully.

DESCRIPTION OF THE PREFERRED EMBODIMENTS

In the following, the method of the present invention is described in more detail.

A copper sulfate recovered from a copper etching waste solution usually contains the mother liquor in the amount of more than 10% by weight, unless it is treated. When the recovered copper sulfate is used as it is for a starting material, the resultant catalyst is very poor in thermal resistance and catalytic lifetime, whereby being unsuitable as a catalyst for practical use.

Copper sulfate recovered from a copper etching waste solution to be used in the present invention is treated with a centrifugal separator, a filter press, or filtration under reduced pressure to reduce the amount of mother liquor to 10% or less. In particular, the treatment using a centrifugal separator is most preferable and effective.

The zinc source used in the present invention can include zinc oxide, zinc sulfate and zinc nitrate; the aluminum source can include alumina sol, aluminum sulfate and aluminum nitrate, and the boron source can include boric acid and borax.

In the preparation of the catalyst precursor of the present invention, the precipitant, which is, if necessary, added to an aqueous metal salt solution of the above components, is a carbonate or bicarbonate of an alkali metal or ammonium. In addition, a combination of alkali hydroxide and carbon dioxide gas can be used as the precipitant. The amount of the precipitant is 1 to 2-fold, preferably 1.1 to 1.5-fold of the equivalent of the copper sulfate. The temperature for forming precipitates is 20° to 90° C., preferably 35° to 80° C. During this procedure, the concentrations of a water-soluble metal salt and the precipitant can be varied over a wide range, but the concentration of 0.2 to 3.0 moles/liter, preferably 0.5 to 2 moles/liter is advantageous industrially.

The precipitates of the metal carbonate salt obtained by the above procedure are then filtered and washed. During this procedure, the amount of sulfur in the precipitates must be decreased within an allowable amount because the copper sulfate is used as a copper source to prepare a catalyst precursor, and a residual sulfur component in the precursor becomes a catalyst poison in a methanol synthetic reaction.

For that purpose, it is important to select the precipitate-forming conditions or washing conditions of a precipitated cake, and thus, the following methods are employed.

The water content of the precipitated cake is controlled to 50 to 80% by weight, preferably 60 to 75% by weight, and a dilute aqueous alkaline solution is used as the washing liquid.

As an alkaline component in the washing liquid, any material which can be removed from the catalyst in the final form to be used or which have no harm to the catalyst can be used. The washing liquid includes an aqueous solution of an alkaline metal compound such as $Na_2CO_3$, $NaHCO_3$ and NaOH, and an aqueous solution of $NH_3$ or $NH_4HCO_3$.

The concentration of the alkaline component in the washing liquid can be varied depending on the compound to be used, but it should preferably be in the range of 0.01 to 0.5% by weight. In addition, the amount of washing liquid to be used can be varied depending on the filtration method, but should preferably be 5 to 15 liters per one mole of the metal carbonate of the precipitated cake.

It is also effective that the precipitated cake was washed with the dilute aqueous alkaline solution, subsequently washed with a dilute aqueous acid solution of an organic acid or nitric acid, and then further washed with pure water. The concentration of the dilute aqueous acid solution can be varied depending on the kind of the acid, but it should preferably be 0.005 to 0.5% by weight.

By the method described above, the sulfur content remaining in a metal carbonate which is the catalyst precursor of the present invention can be reduced to 50 ppm or less with an alkaline metal content of 300 ppm or less.

When preparing the catalyst precursor according to the present invention, there are cases in which the precipitated component comprises a carbonate cake composed of copper, zinc and aluminum compounds, if necessary, and boron compounds, and in which it comprises a carbonate cake composed of copper and zinc compounds, and optionally, and boron compounds. In the former case, the cake can be used as it is in the subsequent step, but in the latter case, the cake is used in the subsequent step after adding an aluminum component in the form of, e.g. alumina sol thereto and then kneading it.

The catalyst precursor above is dried at a temperature of 80° to 120° C., and is then sintered at 280° to 500° C., preferably 300° to 450° C. in an atmosphere of air. Thereafter, a catalyst for practical use can be produced via conventionally known means such as molding.

The composition of the catalyst prepared by the present method is in the range of 0.2 to 12:1, preferably 0.3 to 7:1 in terms of the atomic ratio of copper:zinc.

In the case of a ternary catalyst comprising copper-zinc-aluminum, the contents of each component are, in terms of atomic percentage, 45 to 80%, preferably 50 to 70% of copper, 15 to 50%, preferably 20 to 45% of zinc, and 1 to 20%, preferably 4 to 16% of aluminum.

In the case of a quaternary catalyst comprising copper-zinc-aluminum-boron, the contents of each component are, in terms of atomic percentage, 45 to 80%, preferably 50 to 70% of copper, 15 to 50%, preferably 20 to 45% of zinc, 1 to 16%, preferably 3 to 12% of aluminum and 0.3 to 5%, preferably 0.5 to 3% of boron.

In the catalyst of the present invention, an oxide precursor of magnesium, zirconium, lanthanum, manganese, chromium and silicon, for example, hydroxides and carbonates, or oxyacid salt of phosphor may be added, if necessary.

The catalyst prepared by the method of the present invention can be used in the methanol synthetic reaction using synthetic starting gases comprising CO and $H_2$ and/or $CO_2$, after, for example, being activated by reducing it with hydrogen or carbon monoxide. In addition, the catalyst of the present invention can be used in reactions other than the methanol synthetic reaction, such as a CO conversion reaction, hydrogenation reaction, decomposition or reforming of methanol.

The methanol synthetic reaction in the presence of the catalyst of the present invention can be carried out under conditions of a pressure of 20 to300 atm, preferably 30 to 150 atm; a temperature of 150° to 350° C., preferably 200° to 300° C. and a space velocity of 2000 to 50000 $hr^{-1}$.

The present invention provides a method of preparing a methanol synthesis catalyst using copper sulfate recovered from a low-cost copper etching waste solution as the source of copper.

According to the method of the present invention, a catalyst which has excellent characteristics equal to catalysts prepared from an expensive starting material such as conventional metal nitrates etc. can be prepared and the catalyst cost can be reduced greatly, so that its industrial value is markedly great.

The method of the present invention is described in more detail referring to Examples and Comparative examples.

The water used in each Example and Comparative example is ion-exchanged water. In addition, the sulfur content and Na content of the resulting catalyst precursor were measured by the Methylene Blue method and by atomic-absorption spectroscopy, respectively.

The results of methanol synthetic activity and lifetime test for each catalyst obtained in Examples and Comparative examples are shown in Table 1.

EXAMPLE 1

Copper sulfate recovered from a waste solution of a copper etching process was subjected to a centrifugal separation to obtain copper sulfate (pentahydrate) containing the mother liquor in the amount of 2%, and it was used in the following procedure.

Dissolved in 1.5 liters of water were 201.5 g of copper sulfate and 18.75 g of boric acid, and the resulting solution was maintained at 40° C. (Solution A).

Dissolved in 1.2 liters of water was 102.7 g of sodium carbonate and the resulting solution was maintained at 40° C. (Solution B).

Dispersed in 0.5 liter of water was 49.4 g of zinc oxide and the resulting dispersion was maintained at 40° C. (Dispersion C).

Next, Solution A was added to Solution B while stirring, and then Dispersion C was added thereto. Subsequently, $CO_2$ gas was blown thereinto at a rate of 6 liter/hr and the resulting mixture was raised to 80° C. and maintained at that temperature for 30 minutes.

After the reaction was completed, the mixture was cooled to 60° C. and filtered to give a cake having a water content of 70%. Subsequently, it was washed with 12 liters of a 0.02% aqueous sodium carbonate solution and then with 3 liters of water, and the water was drained off to give a cake.

After 39 g of alumina sol ($Al_2O_3$ content of 10%) and 100 g of water were added to 200 g of the cake (water content of 52%), the resulting mixture was kneaded and dried at 90° C. to obtain a dried product.

The sulfur content of the dried product which is used as catalyst precursor was 10 ppm and the Na content was 150 ppm.

Next, the dried product was calcined at 380° C. in a stream of air and it was then pulverized. Then, graphite was added to the resulting powder in the amount of 3% and was molded into a tablet with 6 mm$\phi \times$5 mm in size to give a catalyst.

The composition of the catalyst was 1.33:1:0.03:0.19 in terms of atomic ratio copper:zinc:boron:aluminum (hereinafter called Catalyst A).

EXAMPLE 2

Copper sulfate recovered from the waste solution of a copper etching process was subjected to a centrifugal separation to obtain copper sulfate (pentahydrate) containing the mother liquor in the amount of 6%, and it was used in the following procedure.

Dissolved in 1.5 liters of water were 214 g of copper sulfate (containing 1.6 g of free sulfuric acid) and 18.75 g of boric acid, and the resulting solution was maintained at 40° (Solution A). Dissolved in 1.2 liters of water was 105 g of sodium carbonate and the resulting solution was maintained at 40° C. (Solution B). Dispersed in 0.5 liter of water was 49.4 g of zinc oxide and the resulting dispersion was maintained at 40° C. (Dispersion C).

Using Solution A, Solution B and Dispersion C, a catalyst precursor was prepared in the same manner as in Example 1.

In this case, the sulfur content of the dried product which is used as a catalyst precursor was 18 ppm and the Na content was 200 ppm.

Using the catalyst precursor, a catalyst was prepared in the same manner as in Example 1 (hereinafter called Catalyst B).

EXAMPLE 3

Copper sulfate recovered from the waste solution of a copper etching process was subjected to centrifugal separation to obtain copper sulfate (pentahydrate) containing 10% mother liquor, and it was used in the following procedure.

Dissolved in 1.5 liters of water were 223 g of copper sulfate (containing 2.6 g of free sulfuric acid of) and 18.75 g of boric acid and the resulting solution was maintained at 40° C. (Solution A). Dissolved in 1.2 liters of water was dissolved 106 g of sodium carbonate and the resulting solution was maintained at 40° C. (Solution B). Dispersed in 0.5 liters of water was 49.4 g of zinc oxide and the resulting dispersion was maintained at 40° C. (Dispersion C).

Using Solution A, Solution B and Dispersion C, a catalyst precursor was prepared in the same manner as in Example 1.

In this case, the sulfur content of the dried product which is used as a catalyst precursor was 17 ppm and the Na content was 220 ppm.

Using the catalyst precursor, a catalyst was prepared in the same manner as in Example 1 (hereinafter called Catalyst C).

REFERENCE EXAMPLE

In the same manner as in Example 1, with the exception of using 195 g of copper nitrate instead of the copper sulfate used in Example 1, a catalyst was prepared (hereinafter called Catalyst D).

In this case, no sulfur was contained in the dried product which is used as a catalyst precursor and the Na content was 230 ppm.

This example concerns a catalyst according to the conventional method using copper nitrate as the source of copper and is the standard for methanol synthesis activity and catalyst lifetime test.

COMPARATIVE EXAMPLE 1

As a copper sulfate recovered from a waste solution of a copper etching process, 231 g of copper sulfate (containing 3.6 g of free sulfuric acid) containing 13% mother liquor was used, and Solution A was prepared in the same manner as in Example 1. In addition, in the same manner as in Example 1 with the exception of using 107 g of sodium carbonate, a catalyst was prepared (hereinafter referred to Catalyst E).

In this case, the sulfur content contained in the dried product which is used as a catalyst precursor was 19 ppm and the Na content was 240 ppm.

COMPARATIVE EXAMPLE 2

As a copper sulfate recovered from a waste solution of a copper etching process, 242 g of copper sulfate (containing 4.9 g of free sulfuric acid) containing 17% mother liquor was used, and Solution A was prepared in the same manner as in Example 1. In addition, in the same manner as in Example 1 with the exception of using 109 g of sodium carbonate, a catalyst was prepared (hereinafter referred to Catalyst F).

In this case, the sulfur content of the dried product which is used as a catalyst precursor was 25 ppm and the Na content was 240 ppm.

COMPARATIVE EXAMPLE 3

Dissolved in 1530 g of a waste solution from a copper etching process (201.5 g calculated as copper sulfate, containing 186 g of free sulfuric acid) were 18.75 g of boric acid and the resulting solution was maintained at 40° C. (Solution A). Dissolved in 2 liters of water was 373 g of sodium carbonate and the resulting solution was maintained at 40° C. (Solution B). Dispersed in 0.5 liter of water was 49.4 g of zinc oxide and the resulting dispersion was maintained at 40° C. (Dispersion C).

A catalyst was prepared in the same manner as in Example 1 (hereinafter referred to Catalyst G).

In this case, the sulfur content of the dried product which is used as a catalyst precursor was 250 ppm and the Na content was 670 ppm.

Activity test

Catalysts A to G were classified and unified into 20 to 35 mesh in grain size and packed into a flow-type reactor. After reducing the catalyst, a methanol synthesis activity test was performed using a starting synthetic gas (CO 23%, $H_2$ 69%, $CO_2$ 7%, $CH_4$ 0.5% and $N_2$ 0.5%)

The standard conditions of the methanol synthesis activity test were a pressure of 70 kg/cm$^2$, a space velocity (SV) of 20,000 hr$^{-1}$ and a temperature of 260° C.

To evaluate the lifetime of the respective catalyst quickly, a method was employed whereby methanol synthesis processing was carried out at a temperature of 360° C. for 2 hours, 6 hours and 10 hours, respectively, and after processing the temperature was returned to 260° C. to measure the methanol synthesis activity.

The test results for Catalysts A to G are shown in Table 1.

TABLE 1

| Example No. | Kind of catalyst | Mother liquor content in copper sulfate % | Methanol concentration in formed gas. mole % Processing time (hr) at 360° C. 0 | 2 | 6 | 10 |
|---|---|---|---|---|---|---|
| 1 | A | 2 | 15.7 | 15.0 | 14.8 | 14.5 |
| 2 | B | 6 | 15.3 | 14.4 | 14.0 | 13.6 |
| 3 | C | 10 | 14.7 | 13.2 | 12.7 | 12.0 |
| Ref.* | D | copper nitrate | 15.4 | 15.1 | 14.8 | 14.5 |
| Comparative | | | | | | |
| 1 | E | 13 | 14.0 | 11.2 | 9.0 | 7.6 |
| 2 | F | 17 | 14.0 | 9.1 | 7.2 | 4.5 |
| 3 | G | waste solution | 5.2 | 1.7 | 0.0 | 0.0 |

*Reference example

What is claimed is:

1. A methanol synthesis process comprising reacting a methanol synthesis gas composition comprising $H_2$ and at least one of CO and $CO_2$ in the presence of a methanol synthesis catalyst, wherein the methanol synthesis catalyst comprises 50 to 70 atomic % copper, 20 to 45 atomic % zinc, 3 to 12 atomic % aluminum and 0.5 to 3 atomic % boron and is a catalyst produced by drying and sintering a catalyst precursor, said catalyst precursor is produced from a copper compound, a zinc compound, an aluminum compound and a boron compound, by (a) precipitating from an aqueous reaction mixture comprising a copper sulfate which is recovered from a copper etching waste solution mother liquor, the copper sulfate comprising up to 10% by weight of said mother liquor, with a precipitant, said precipitant being in an amount of 1-fold to 2-fold equivalent of the copper sulfate, said precipitating being carried out in the presence of the boron compound, the boron compound being a water soluble boron compound, and mixing therewith the zinc compound, without separation, to form a precipitate in said reaction mixture, (b) filtering said reaction mixture from step (a) to form a cake, (c) washing said cake from step (b) with an aqueous alkali solution in a concentration of 0.01 to 0.5 weight % and then washing with water, (d) adding said aluminum compound to said washed cake of step (c), (e) kneading the resulting mixture form step (d) and (f) drying the resulting kneaded mixture from step (e).

2. The process according to claim 1, wherein the drying is carried out at a temperature of 80° to 120° C. and the sintering is carried out at a temperature of 300° to 450° C. in an atmosphere of air.

3. The process according to claim 2, wherein the synthesis gas composition comprises CO and $H_2$ and optionally $CO_2$ and the methanol synthesis is carried out at a pressure of 20 to 300 atm, a temperature of 150° to 350° C. and a space velocity of 2,000 to 50,000 hour$^{-1}$.

4. The process according to claim 3, wherein the methanol synthesis is carried out at a pressure of 30 to 150 atm and a temperature of 200° to 300° C.

5. The process according to claim 4, wherein the precipitating step is carried out at a temperature of 20° to 90° C.

6. The process according to claim 5, wherein the concentration of the precipitant is 0.2 to 3.0 moles/liter.

7. The process according to claim 6, wherein the cake prior to being washed has a water content of 50 to 80 weight % of said cake.

8. The process according to claim 7, wherein the zinc compound is selected from the group consisting of zinc oxide, zinc sulfate and zinc nitrate; the aluminum compound is selected from the group consisting of alumina sol, aluminum sulfate and aluminum nitrate; and the boron compound is selected from the group consisting of boric acid and borax.

9. The process according to claim 8, wherein the precipitant is in an amount of 1.1-fold to 1.5-fold equivalent of the copper sulfate.

10. The process according to claim 9, wherein the temperature for conducting the precipitating step is 35° to 80° C., the concentration of the precipitant is 0.5 to 2 moles/liter and the precipitant is selected from the group consisting of a carbonate of an alkali metal, a bicarbonate of an alkali metal, a carbonate of ammonium, a bicarbonate of ammonium and a combination of an alkali hydroxide and carbon dioxide.

11. The process according to claim 10, wherein the cake prior to being washed has a water content of 60 to 75% by weight of said cake.

12. The process according to claim 1, wherein the aqueous alkali solution comprises a compound selected from the group consisting of $Na_2CO_3$, $NaHCO_3$, NaOH, $NH_3$ and $NH_4HCO_3$.

13. The process according to claim 12, which further comprises washing the cake with a dilute aqueous acid solution of an organic acid or nitric acid solution after said washing with dilute aqueous alkaline solution and before said washing with water, the acid having a concentration of 0.005 to 0.5% by weight.

14. A methanol synthesis process comprising reacting a methanol synthesis gas composition comprising $H_2$ and at least one of CO and $CO_2$ in the presence of a methanol synthesis catalyst, wherein the methanol synthesis catalyst comprises 50 to 70 atomic % copper, 20 to 45 atomic % zinc, 3 to 12 atomic % aluminum and 0.5 to 3 atomic % boron and is a catalyst produced by drying and sintering a catalyst precursor, said catalyst precursor is produced from a copper compound, a zinc compound, an aluminum compound and a boron compound, by (a) precipitating from an aqueous reaction mixture comprising a copper sulfate which is recovered from a copper etching waste solution mother liquor, the copper sulfate comprising up to 10% by weight of said mother liquor, with a precipitant, said precipitant being in an amount of 1-fold to 2-fold equivalent of the copper sulfate, said precipitating being carried out in the presence of the boron compound, the boron compound being a water soluble boron compound, and mixing therewith the zinc compound and said aluminum compound, without separation, to form a precipitate in said reaction mixture, (b) filtering said reaction mixture from step (a) to form a cake, (c) washing said cake from step (b) with an aqueous alkali solution in a concentration of 0.01 to 0.5 weight % and then washing with water, and (d) drying the resulting material from step (c).

15. The process according to claim 14, wherein the drying is carried out at a temperature of 80° to 120° C. and the sintering is carried out at a temperature of 300° to 450° C. in an atmosphere of air.

16. The process according to claim 15, wherein the synthesis gas composition comprises CO and $H_2$ and optionally $CO_2$ and the methanol synthesis is carried out at pressure of 20 to 300 atm, a temperature of 150° to 350° C. and a space velocity of 2,000 to 50,000 $hour^{-1}$.

17. The process according to claim 16, wherein the methanol synthesis is carried out at a pressure of 30 to 150 atm and a temperature of 200° to 300° C.

18. The process according to claim 17, wherein the precipitating step is carried out at a temperature of 20° to 90° C.

19. The process according to claim 18, wherein the concentration of the precipitant is 0.2 to 3.0 moles/liter.

20. The process according to claim 19, wherein the cake prior to being washed has a water content of 50 to 80 weight % of said cake.

21. The process according to claim 20, wherein the zinc compound is selected from the group consisting of zinc oxide, zinc sulfate and zinc nitrate; the aluminum compound is selected from the group consisting of alumina sol, aluminum sulfate and aluminum nitrate; and the boron compound is selected from the group consisting of boric acid and borax.

22. The process according to claim 21, wherein the precipitant is in an amount of 1.1-fold to 1.5-fold equivalent of the copper sulfate.

23. The process according to claim 22, wherein the temperature for conducting the precipitating step is 35° to 80° C., the concentration of the precipitant is 0.5 to 2 moles/liter and the precipitant is selected from the group consisting of a carbonate of an alkali metal, a bicarbonate of an alkali metal, a carbonate of ammonium, a bicarbonate of ammonium and a combination of an alkali hydroxide and carbon dioxide.

24. The process according to claim 23, wherein the cake prior to being washed has a water content of 60 to 75% by weight of said cake.

25. The process according to claim 24, wherein the aqueous alkali solution comprises a compound selected from the group consisting of $Na_2CO_3$, $NaHCO_3$, NaOH, $NH_3$ and $NH_4HCO_3$.

26. The process according to claim 25, which further comprises washing the cake with a dilute aqueous acid solution of an organic acid or nitric acid solution after said washing with dilute aqueous alkaline solution and before said washing with water, the acid having a concentration of 0.005 to 0.5% by weight.

* * * * *